(12) United States Patent
Klein

(10) Patent No.: US 7,688,942 B2
(45) Date of Patent: Mar. 30, 2010

(54) ELEMENT ANALYSIS DEVICE

(75) Inventor: Albert Klein, Simmersfeld (DE)

(73) Assignee: Elisabeth Katz, Simmersfeld (DE)

( * ) Notice: Subject to any disclaimer, the term of this patent is extended or adjusted under 35 U.S.C. 154(b) by 359 days.

(21) Appl. No.: 11/578,537

(22) PCT Filed: Apr. 15, 2005

(86) PCT No.: PCT/EP2005/003976

§ 371 (c)(1),
(2), (4) Date: Aug. 30, 2007

(87) PCT Pub. No.: WO2005/100963

PCT Pub. Date: Oct. 27, 2005

(65) Prior Publication Data
US 2008/0212736 A1  Sep. 4, 2008

(30) Foreign Application Priority Data
Apr. 17, 2004  (DE) ................. 10 2004 019 030

(51) Int. Cl.
G01N 23/223 (2006.01)
G01T 1/36 (2006.01)

(52) U.S. Cl. ........................... 378/44; 250/400
(58) Field of Classification Search ............ 378/44–50; 250/399–400
See application file for complete search history.

(56) References Cited

U.S. PATENT DOCUMENTS

| | | | |
|---|---|---|---|
| 3,710,104 A | | 1/1973 | Pavlik |
| 3,889,113 A | * | 6/1975 | Rhodes ........................ 378/45 |
| 4,185,202 A | * | 1/1980 | Dean et al. .................... 378/34 |
| 4,484,339 A | * | 11/1984 | Mallozzi et al. .............. 378/82 |
| 5,740,223 A | * | 4/1998 | Ozawa et al. ................ 378/161 |
| 6,052,429 A | * | 4/2000 | Ohno et al. .................... 378/45 |
| 6,233,307 B1 | * | 5/2001 | Golenhofen ................... 378/45 |
| 6,314,158 B1 | * | 11/2001 | Shiota et al. .................. 378/48 |
| 6,590,955 B2 | * | 7/2003 | Matoba et al. ................ 378/44 |

(Continued)

FOREIGN PATENT DOCUMENTS

DE  102 30 990 A1  2/2004

OTHER PUBLICATIONS

Patent Abstract of Japan No. 2002-303593 A (Oct. 18, 2002).

*Primary Examiner*—Edward J Glick
*Assistant Examiner*—Anastasia Midkiff
(74) *Attorney, Agent, or Firm*—Rabin & Berdo, PC

(57) ABSTRACT

Described is an element analysis device, which can be used to obtain precise measurements even under unfavorable environmental conditions. For this, the device is provided with a transporting means with a measuring region (14) for transporting the substance (S) to be measured, an excitation source with an exit window located in a first case (22) and an X-ray fluorescence detector (30) that is directed toward the measuring region (14), as well as an entrance window (34) that is located in a second case (32). To minimize the air absorption and prevent dust and dirt from being deposited, a tube (40, 50) extends from the entrance window (34) and/or the exit window (24) in the direction of the measuring region, which tube is essentially tightly connected to the respective case (22, 32) and is open at the end facing the measuring region and is provided with a connection (44, 54) for feeding a flushing gas into the tube (FIG. 1).

27 Claims, 4 Drawing Sheets

Figure 1:
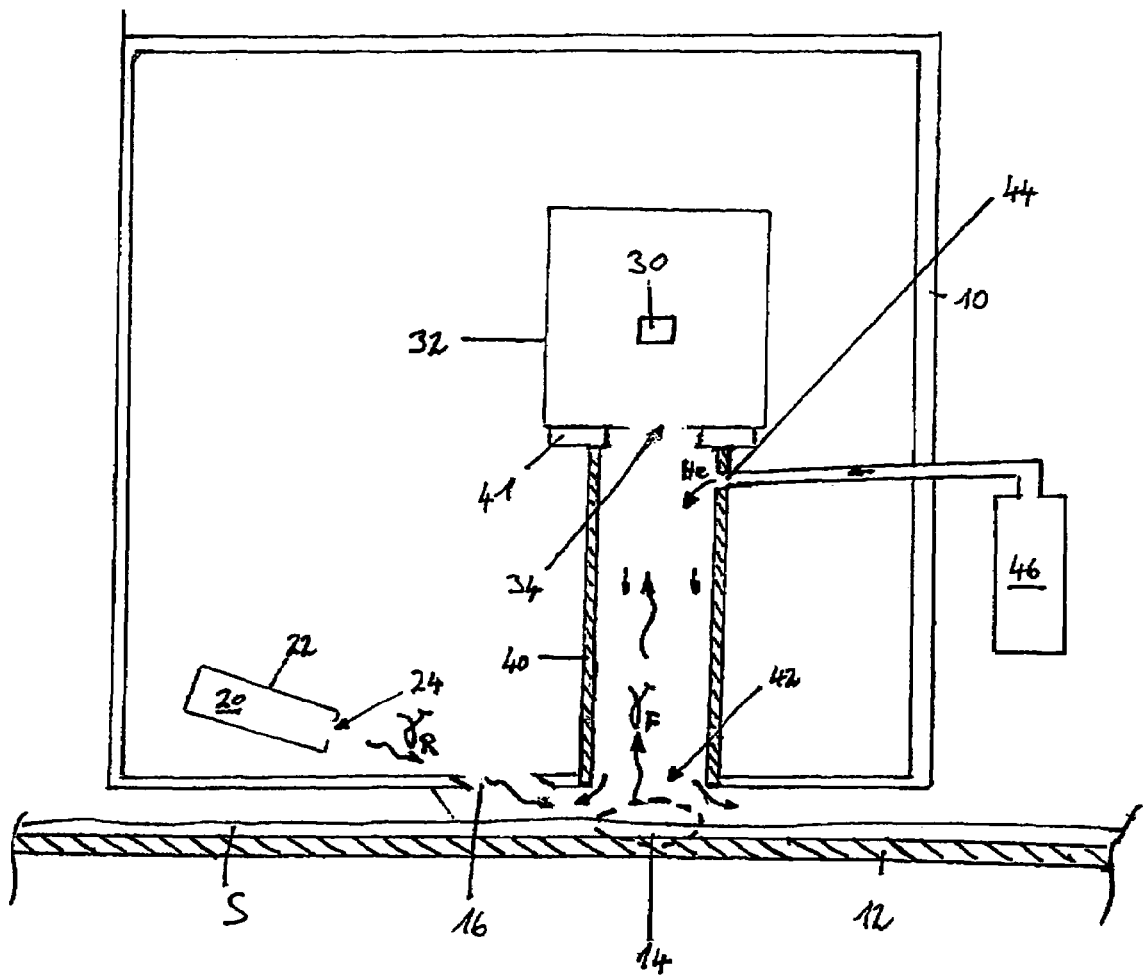

U.S. PATENT DOCUMENTS 7,432,501 B2 * 10/2008 Bateman et al. ............. 250/294
2003/0133536 A1 * 7/2003 Kuwabara et al. ............. 378/44
2003/0152192 A1 8/2003 Hasegawa
2006/0262900 A1 * 11/2006 Sipila et al. ................... 378/44

* cited by examiner

ELEMENT ANALYSIS DEVICE

TECHNICAL FIELD OF INVENTION

The invention relates to an element analysis device, as defined in the preamble to claim 1.

For example in the field of mining and metallurgy, it is frequently necessary to measure continuously (online) the share of specific elements in a substance. For this, the substance is transported past a respective measuring device while positioned on a conveyor belt or the like. A frequently used measuring method in that case is the X-ray fluorescence spectroscopy. The device for realizing this measuring method comprises an excitation source, which irradiates a measuring region on the conveyor belt with fluorescence-exciting radiation. The fluorescence-exciting radiation for the most part involves gamma rays or X-rays. The measuring device is furthermore provided with an X-ray fluorescence detector for spectrally measuring the X-ray fluorescence radiation emitted by the substance, wherein the measuring result is then used to compute the share of specific elements with the aid of known methods.

However, various measuring-technical problems occur when using this measuring method, especially in the industrial sector. The first problem is that lightweight elements such as aluminum must frequently be measured. However, the X-ray fluorescence radiation of these elements is relatively long-wave and is therefore absorbed not only by detector windows, but is absorbed strongly by a few centimeters of air already. Connected to this problem is the second problem that the measuring environment is frequently dirty and dusty, thus further reducing the radiation transmission in air, so that the entrance window and the exit window are quickly covered with an absorbent layer. A third problem is that for some application cases, the substances to be measured are relatively hot and that the heat radiation reduces the function of the X-ray fluorescence detector.

PRIOR ART

A measuring device of the generic type is known from Reference WO 00/16078, which proposes arranging the X-ray fluorescence detector near—within 5 cm of—the surface of the substance to be measured to solve the problem of strong air absorption. To be sure, this measure allows minimizing the air absorption, but the problem of radiation-dampening dust deposits still remains. Furthermore, hot substances cannot be measured at all or only with great difficulty with a measuring device as proposed in this document, because the close proximity of the X-ray fluorescence detector to the surface of the substance does not allow the detector to reach the required low operating temperature.

SUBJECT MATTER OF THE INVENTION

Starting from this point, it is the object of the present invention to improve a generic device of this type, such that it can also be used under unfavorable environmental conditions. In particular, the measuring device must also be suitable for use in a dusty and dirty environment and for measuring hot substances.

This object is solved with a device having the features as defined in claim 1.

The basic idea behind the invention is to guide the exciting and/or fluorescent radiation to the area near the surface of the substance to be measured inside a tube, which tube is open on the end facing the measuring region. The tube is flushed with gas, which exits the tube in the direction of the measuring region, thereby preventing any dust deposits.

In particular for the measuring of lightweight elements, helium is preferably used as flushing gas since the absorption in helium is considerably lower than in air because of its lower density. The tube must be open toward the bottom in that case and should preferably be arranged substantially vertically. This arrangement has the further advantage that owing to the low absorption of the helium, the X-ray fluorescence detector can be arranged relatively far from the substance to be measured, so that even a relatively high temperature of the substance to be measured does not present a problem. Arranging the X-ray fluorescence detector at a distance that is relatively far from the surface of the substance to be measured furthermore has the advantage that certain fluctuations in the surface height have only a slight effect on the intensity of the radiation impinging on the X-ray fluorescence detector because of the square law.

Preferred embodiments of the invention follow from the dependent claims and the exemplary embodiments, shown in further detail in the Figures, wherein these show in:

SHORT DESCRIPTION OF THE DRAWINGS

Figure 2:
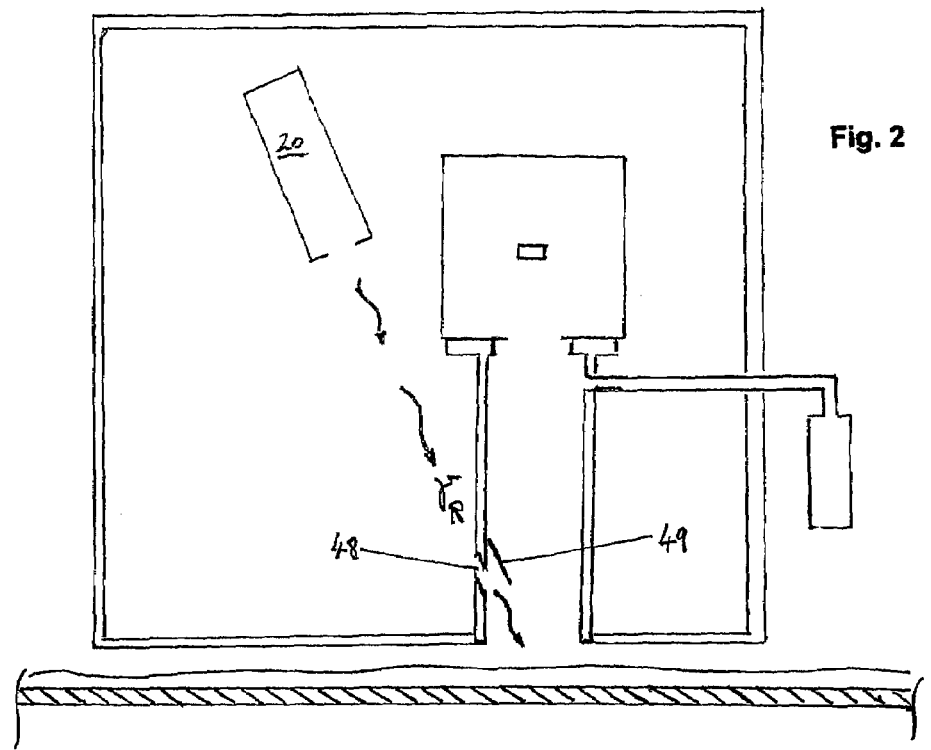
Figure 4:
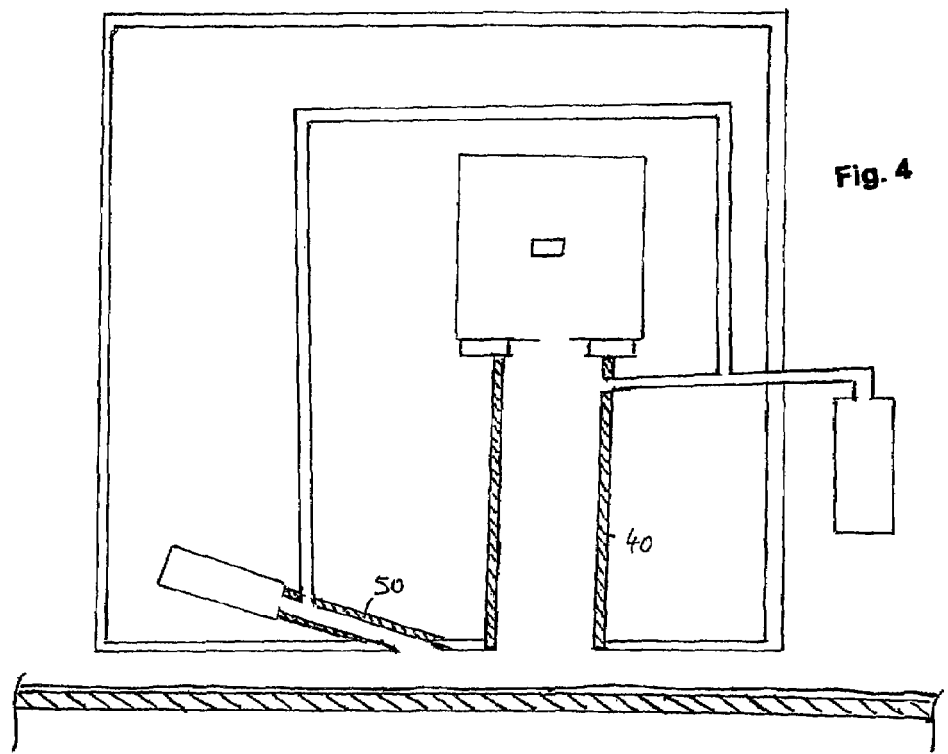
Figure 3:
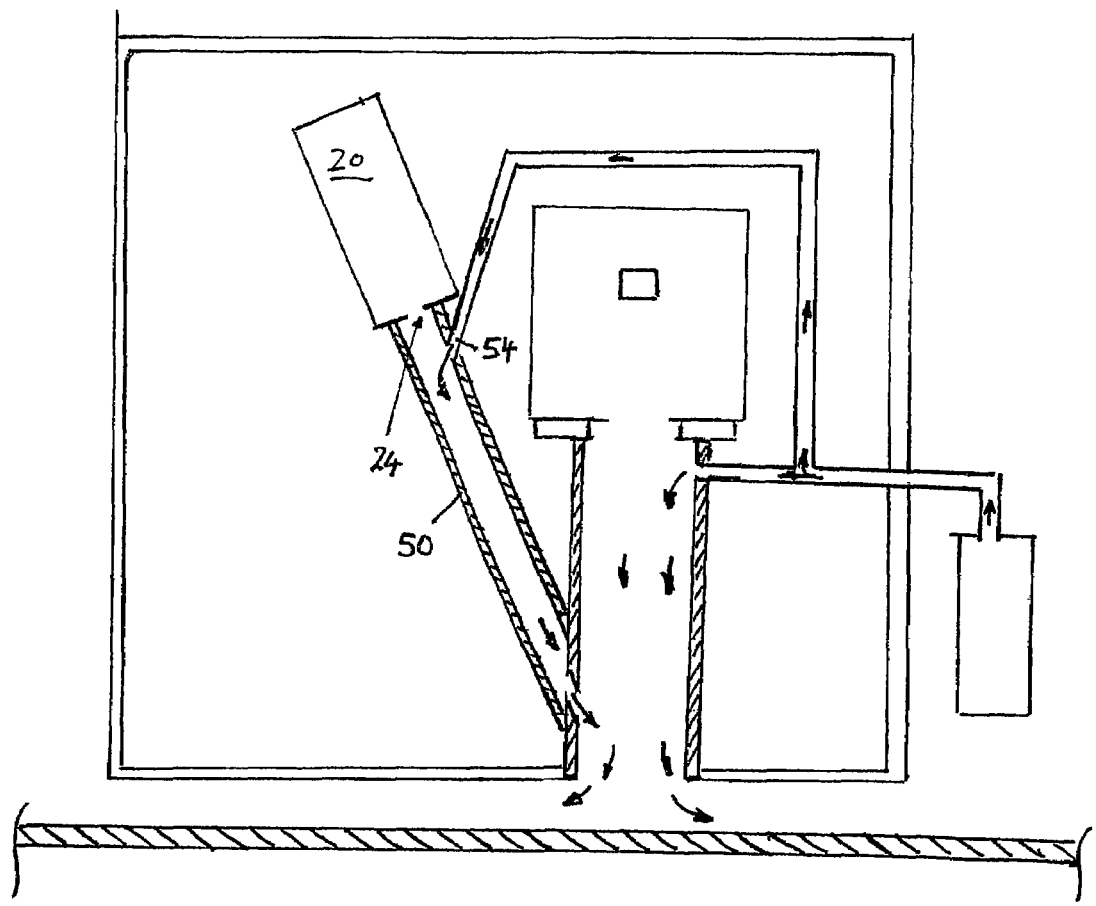
Figure 5:
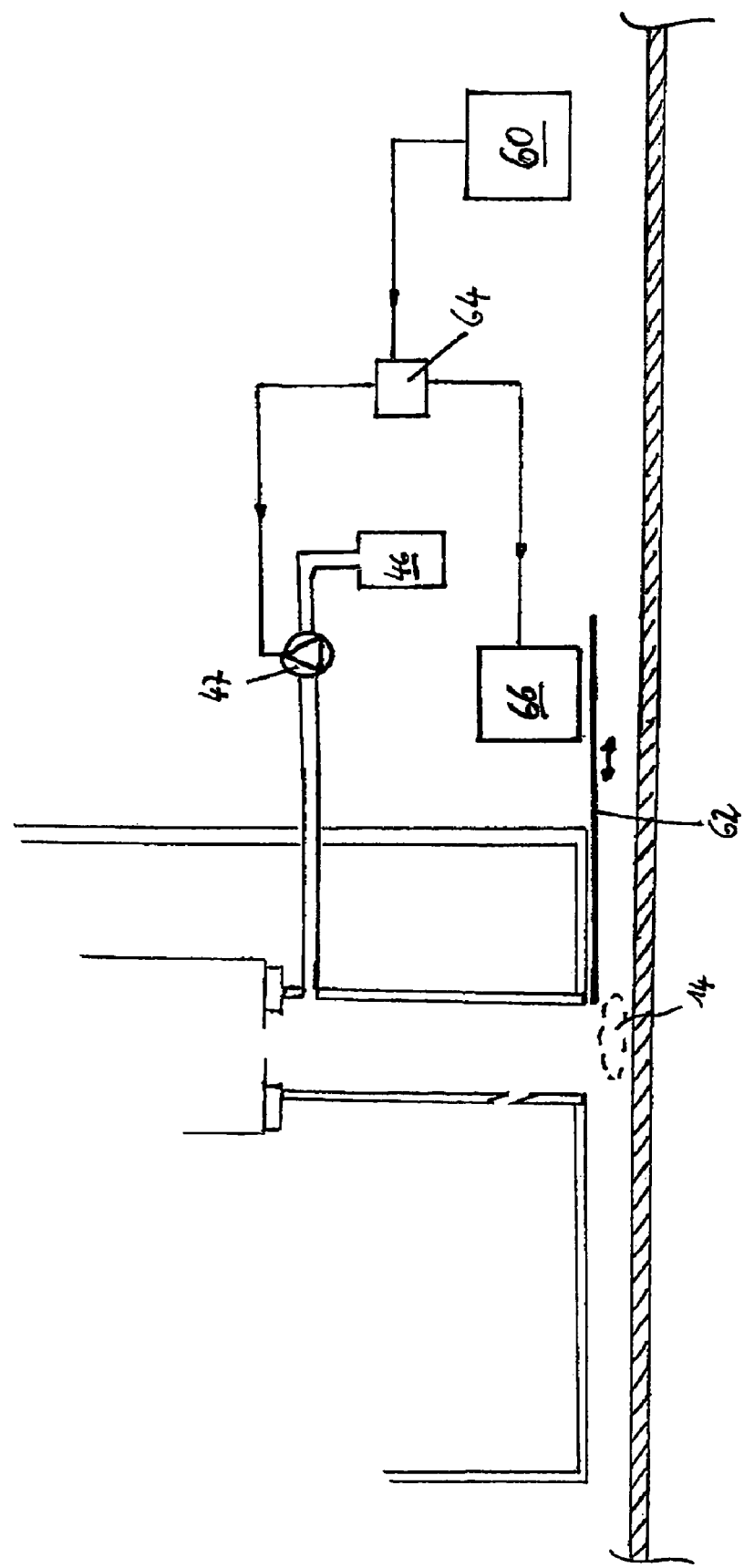

FIG. 1 A schematic representation of a first embodiment of the invention;

FIG. 2 A schematic representation of a second embodiment of the invention;

FIG. 3 A schematic representation of a third embodiment of the invention;

FIG. 4 The schematic representation of a fourth embodiment of the invention;

FIG. 5 The embodiment shown in FIG. 2 with an added material sensor.

DESCRIPTION OF PREFERRED EMBODIMENTS

FIG. 1 shows a first exemplary embodiment, for which an outer case 10 is arranged above the conveyor belt 12, which serves as a transporting means for this embodiment and conveys the substance S to be measured. Inside this outer case 10, an X-ray tube 20 that functions as an excitation source is installed inside a first case 22. An X-ray beam $y_R$ that is directed so as to impinge on a measuring region 14 passes through an exit window 24 in the first case 22. Since the outer case 10 as a rule has relatively thick walls, for example is composed of stainless steel, the case underside is provided with an exit opening 16 for the X-ray radiation. To prevent dust and other particles from entering the inside of the outer case 10, the exit opening is covered with a window, for example a beryllium film.

As a result of this irradiation, X-ray fluorescence radiation $y_F$ is generated in the measuring region 14, which is then measured by the X-ray fluorescence detector 30 that is also located inside the outer case 10. From the second case 32 of the X-ray fluorescence detector 30, a first tube 40 extends vertically downward and is open at its lower end. The first tube 40 is connected via a rubber bellows 41 to the second case 32 of the X-ray fluorescence detector 30, wherein this connection is substantially gastight. The first tube 40 is composed totally or in part of zirconium. The use of an elastic rubber bellows serves to mechanically uncouple the first tube 40 from the X-ray fluorescence detector 30. This is necessary since most X-ray fluorescence detectors are mechanically relatively sensitive. At its lower end, the first tube 40 is tightly connected to the outer case 10.

The X-ray fluorescence radiation generated in the measuring region 14 travels through the tube opening 42 into the first tube 40 and then travels through this tube to the entrance window 34, through which it enters the X-ray fluorescence detector 30. The entrance window 34 in that case can be open or can be covered with a film, for example, depending on the detector used.

Figure 1A:
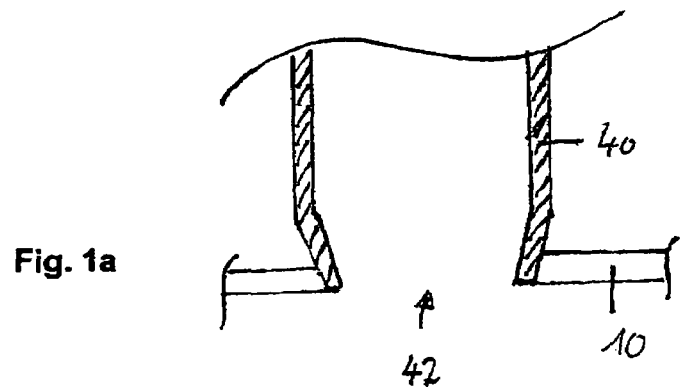

To prevent dust, ashes, or similar material from absorbing the X-ray fluorescence radiation along its path from the measuring region 14 to the X-ray fluorescence detector 30, the first tube 40 is flushed with helium. For this, the first tube 40 is provided with a connection 44, which connects the tube 40 to a helium source 46 that is usefully located outside of the outer case 10. The connection 44 is preferably located in an upper section of the tube 40, near the entrance window 34. The helium flows from the connection 44 into the tube 40 where it flows in downward direction and subsequently leaves the tube 40 through the tube opening 42. To achieve maximum intensity, the tube diameter should at least match the diameter of the measuring sensitive surface of the detector that is used. The tube preferably has an inside diameter of 10 to 50 mm. A relatively large tube diameter is furthermore important, so that the flushing gas connection can be attached. To reach high flow speeds for the flushing gas at the tube opening, it may be useful to taper the tube toward the tube opening (FIG. 1*a*).

It is furthermore possible to arrange the exit opening 16 immediately adjacent to the tube opening 42, so that the exit opening 16 can also be flushed with helium. It may be useful in that case to expand the tube 40 toward the tube opening 42. In particular, it may be favorable in that case to embody the region around the tube opening 42 asymmetrical, such that flushing gas exiting the tube opening 42 is guided in the direction of the exit opening 16.

Since helium is considerably lighter than air, a helium column is always present in the tube 40 to prevent air from entering. The use of a helium flushing operation thus has several effects. On the one hand, no window film or only an extremely thin window film is needed at the entrance window 34 of the X-ray fluorescence detector 30, thereby resulting in a very low absorption by the measuring device itself. On the other hand, it prevents the depositing of dust, ashes, and the like on the window film, as well as the presence of dust, ashes, and the like in a large portion of the beam path for the X-ray fluorescence radiation. This not only reduces the total absorption, but also prevents absorption fluctuations, which could hinder the measuring operation in a manner that it is hard to reproduce. Finally, a large portion of the radiation path is free of air, which also contributes to a strong reduction in the total absorption. Furthermore, the spectral absorption of some air constituents, for example argon, is strongly reduced in some application cases. This effect can be important, particularly when measuring elements that are located adjacent to the absorbing constituent in the periodic system.

With the exemplary embodiment shown in FIG. 1, it is possible for particles to be deposited on the cover for the exit opening 16. Because of the at least relatively high energy of the X-rays used, this is not very critical with regard to the required intensity, but can still lead to a distortion of the measuring result. In the exemplary embodiment shown in FIG. 2, the beam path of the exciting X-ray radiation therefore passes through the walls of the first tube 40. In that case, the first tube 40 can be produced from a material that is pervious to the exciting X-ray radiation. Rubber is one example for such a material, wherein rubber furthermore has the advantage of not transmitting vibrations to the X-ray fluorescence detector 30 even without installing a special rubber bellows in-between. A different option is shown in FIG. 2 and consists of providing an opening 48 in the wall of the first tube 40, through which the exciting X-ray radiation enters the first tube 40. The opening 48 can be covered with a window, for example a beryllium film, to prevent leakage of the helium through this opening 48. To minimize the measuring background, the window can also be replaced with a filter, through which only photons above a cutoff energy can travel. To further minimize scattering, an aperture 49 is preferably arranged above the opening 48, for example an aperture of zirconium. As alternative to the embodiment shown in FIG. 2, the opening 48 can also be arranged directly adjacent to the tube end, so that it extends in the form of a recess from the open tube end into the tube wall. It is furthermore possible to connect the opening 48 and the exit window 24 of the X-ray tube with an X-ray conductor. The aperture 49 is located directly at the recess or opening 48 and is aligned parallel to the direction of irradiation for the excitation source.

With the exemplary embodiment shown in FIG. 3, not only the largest portion of the beam path for the X-ray fluorescence radiation, but also the largest portion of the exciting X-ray radiation is located inside a helium-flushed tube. According to the exemplary embodiment shown in FIG. 2, the X-ray radiation coming from the X-ray tube 20 enters through the opening 48 into the first tube 40. The second tube 50, which is also connected via a different connection 54 to the helium source 46, is located between this opening 48 and the exit window 24 in the X-ray tube 20. As a result, the interfering absorption by air can be prevented in some cases. As an alternative to the embodiment shown in FIG. 3, it is also conceivable to keep the first and second tube completely separate, as shown in FIG. 4.

To keep the operating costs as low as possible, the tube or tubes should be flushed with helium only during the active measuring operation. According to FIG. 5, a material sensor 60 that is installed upstream of the measuring region 14 is therefore proposed, which sensor detects whether or not the conveyor belt contains a substance to be measured. The signals from this material sensor 60 are transmitted to the control unit 64. If no substance is detected on the conveyor belt, then the measurement is ended, if necessary with a time delay, and the valve 47 is closed. To prevent dirt from entering the first tube 40 during the time when no helium flushing takes place, a shutter 62 that is operated by a motor 66 is provided at the tube opening 42. The shutter closes off the tube end once the valve 47 is closed.

If a substance is again detected on the conveyor belt 12, then the shutter 62 and the valve 47 are opened. As a result, the first tube 40 is pre-flushed, until the substance reaches the measuring region 14 and the measuring operation starts or is continued.

The main object of the above-described exemplary embodiments is to reduce the absorption of X-ray fluorescence radiation. To be sure, in most application cases this will be the most important point, but the herein described principle of the "open gas flushing" can also be used, for example, exclusively for the beam path of the exciting radiation.

REFERENCE NUMBER LIST

10 outer case
12 conveyor belt
14 measuring region
16 exit opening
20 X-ray tube
22 first case
24 exit window 30 X-ray fluorescence detector
32 second case
34 entrance window
40 first tube
41 rubber bellows
42 tube opening
44 connection
46 helium source
47 valve
48 opening
49 aperture
50 second tube
54 additional connection
60 material sensor
62 shutter
64 control unit
66 motor
S substance

The invention claimed is:

1. An element analysis device for analyzing a substance, said device comprising:
    a transporting means with a measuring region, for transporting the substance to be measured;
    an outer case;
    a first case having an exit window, the first case being disposed inside the outer case;
    a second case having an entrance window, the second case being disposed inside the outer case;
    at least one excitation source located in the first case the excitation source being oriented such that a fluorescence-exciting radiation from the excitation source impinges on the measuring region;
    at least one X-ray fluorescence detector located in the second case, the X-ray fluorescence detector being oriented toward the measuring region; and
    a tube extending from the entrance window of the second case in a direction of the measuring region, the tube being essentially tightly connected to the second case and to the outer case, wherein
        the tube is completely open at an end facing the measuring region, and is provided with a connection for feeding a flushing gas into the tube, such that the flushing gas freely exits the outer case via the end of the tube facing the measuring region, thereby preventing dust from entering the tube.

2. The device according to claim 1, wherein the tube extends downward from the second case.

3. The device according to claim 1, wherein the connection is located near the entrance window or the exit window.

4. The device according to claim 1, wherein helium is used as the flushing gas.

5. The device according to claim 1, wherein the excitation source is an X-ray tube.

6. The device according to claim 1, wherein the excitation source comprises a gamma-radiator.

7. The device according to claim 1, wherein the tube is connected to the detector with the aid of an elastic material, such that it does not vibrate.

8. The device according to claim 1, wherein the tube is narrowed down at its end facing the measuring region.

9. The device according to claim 1, wherein the tube is tightly connected to the second case for the fluorescence detector and at least in some sections is pervious to the fluorescence exciting radiation.

10. The device according to claim 1, wherein the tube leading to the X-ray fluorescence detector is composed totally or in part of zirconium.

11. The device according to claim 1, wherein the tube is tightly connected to the second case and that an inside diameter of the tube is at least the same size as a diameter of a measuring-sensitive surface of the X-ray fluorescence detector.

12. The device according to claim 1, wherein a material sensor and a shut-off device for a supply of the flushing gas are provided and that the supply of the flushing gas is shut off in an absence of a material to be measured.

13. An element analysis device for analyzing a substance, comprising:
    a transporting means with a measuring region, for transporting the substance to be measured;
    an outer case;
    at least one excitation source with an exit window, located in a first case, wherein the excitation source is oriented such that a fluorescence-exciting radiation from the excitation source impinges on the measuring region, wherein the first case is arranged inside the outer case; and
    at least one X-ray fluorescence detector that is oriented toward the measuring region and comprises an entrance window, located in a second case, wherein the second case is arranged inside the outer case,
    wherein a tube extends from the entrance window in the direction of the measuring region, wherein this tube is essentially tightly connected to the second case and to the outer case and is open at the end facing the measuring region, and is provided with a connection for feeding a flushing gas into the tube;
    wherein the tube is tightly connected to the second case for the fluorescence detector and at least in some sections is pervious to the fluorescence exciting radiation; and
    wherein the complete tube is pervious to the fluorescence exciting radiation.

14. The device according to claim 13, wherein the tube consists of an elastic material.

15. The device according to claim 9, wherein a recess extends from the open tube end into the tube wall.

16. The device according to claim 9, wherein near the open tube end, an opening is provided in the tube wall.

17. The device according to claim 16, wherein the opening is slot-shaped.

18. The device according to claim 16, wherein the tube is provided with an aperture between the recess or the opening and the X-ray fluorescence detector.

19. The device according to claim 15, wherein the recess or the opening is closed off with a window through which the fluorescence-exciting radiation can pass.

20. The device according to claim 15, wherein a second tube extends from the recess or the opening to the first case for the excitation source.

21. An element analysis device for analyzing a substance, comprising:
    a transporting means with a measuring region, for transporting the substance to be measured;
    an outer case;
    at least one excitation source with an exit window, located in a first case, wherein the excitation source is oriented such that a fluorescence-exciting radiation from the excitation source impinges on the measuring region, wherein the first case is arranged inside the outer case; and
    at least one X-ray fluorescence detector that is oriented toward the measuring region and comprises an entrance window, located in a second case, wherein the second case is arranged inside the outer case, wherein a tube extends from the entrance window in the direction of the measuring region, wherein this tube is essentially tightly connected to the second case and to the outer case and is open at the end facing the measuring region, and is provided with a connection for feeding a flushing gas into the tube;

wherein the tube is tightly connected to the second case for the fluorescence detector and at least in some sections is pervious to the fluorescence exciting radiation;

wherein a recess extends from the open tube end into the tube wall;

wherein a second tube extends from the recess or the opening to the first case for the excitation source; and wherein the second tube is provided with a separate gas flushing.

22. An element analysis device for analyzing a substance, comprising:

a transporting means with a measuring region, for transporting the substance to be measured;

an outer case;

at least one excitation source with an exit window, located in a first case, wherein the excitation source is oriented such that a fluorescence-exciting radiation from the excitation source impinges on the measuring region, wherein the first case is arranged inside the outer case; and at least one X-ray fluorescence detector that is oriented toward the measuring region and comprises an entrance window, located in a second case, wherein the second case is arranged inside the outer case, wherein a tube extends from the entrance window in the direction of the measuring region, wherein this tube is essentially tightly connected to the second case and to the outer case and is open at the end facing the measuring region, and is provided with a connection for feeding a flushing gas into the tube;

wherein the tube is tightly connected to the second case for the fluorescence detector and at least in some sections is pervious to the fluorescence exciting radiation;

wherein a recess extends from the open tube end into the tube wall; and wherein the tube is provided with an aperture between the recess or the opening and the X-ray fluorescence detector.

23. The device according to claim 22, wherein the aperture is located directly at the recess or opening and is aligned parallel to the direction of irradiation for the excitation source.

24. The device according to claim 22, wherein a material sensor and a shut-off device for a supply of the flushing gas are provided and that the supply of the flushing gas is shut off in an absence of a material to be measured.

25. The device according to claim 24, wherein the tube is provided with a closing element at the end facing the measuring region, which closes off the tube when the supply of the flushing gas is cut off.

26. The device according to claim 24, wherein a pre-flushing phase is initiated once the material detector responds and before starting measuring the substance.

27. The device according to claim 26, wherein the material sensor is located far enough away from the measuring region, so that a time needed for transporting the material to the measuring region is sufficient for realizing a pre-flushing operation.

* * * * *